United States Patent
Weidl et al.

(10) Patent No.: US 10,140,532 B2
(45) Date of Patent: Nov. 27, 2018

(54) METHOD AND DEVICE FOR MONITORING AT LEAST ONE VEHICLE OCCUPANT, AND METHOD FOR OPERATING AT LEAST ONE ASSISTANCE DEVICE

(75) Inventors: Galia Weidl, Boeblingen (DE); Ralf Herrtwich, Kleinmachnow (DE); Michael Schrauf, Esslingen (DE)

(73) Assignee: Daimler AG, Stuttgart (DE)

(*) Notice: Subject to any disclaimer, the term of this patent is extended or adjusted under 35 U.S.C. 154(b) by 511 days.

(21) Appl. No.: 14/111,440

(22) PCT Filed: Dec. 9, 2011

(86) PCT No.: PCT/EP2011/006209
§ 371 (c)(1),
(2), (4) Date: Dec. 24, 2013

(87) PCT Pub. No.: WO2012/139619
PCT Pub. Date: Oct. 18, 2012

(65) Prior Publication Data
US 2014/0104405 A1    Apr. 17, 2014

(30) Foreign Application Priority Data
Apr. 12, 2011 (DE) .................. 10 2011 016 772

(51) Int. Cl.
*G06K 9/00* (2006.01)
*A61B 5/024* (2006.01)
(Continued)

(52) U.S. Cl.
CPC ...... *G06K 9/00845* (2013.01); *A61B 5/02416* (2013.01); *A61B 5/18* (2013.01);
(Continued)

(58) Field of Classification Search
CPC ............ G06K 9/00845; G06K 9/00832; A61B 5/02416; A61B 5/18
(Continued)

(56) References Cited

U.S. PATENT DOCUMENTS

| 5,729,619 A | 3/1998 | Puma |
| 2008/0214944 A1* | 9/2008 | Morris .................. A61B 5/165 600/509 |

(Continued)

FOREIGN PATENT DOCUMENTS

| DE | 10 2009 016 936 A1 | 11/2009 |
| EP | 1 182 089 A2 | 2/2002 |

(Continued)

OTHER PUBLICATIONS

Cortés F, Aranda JM, Sanchez-Reillo R, Meléndez J, López F. Spectral Selection for a Biometric Recognition System Based on Hand Veins Detection Through Image Spectrometry. InBIOSIG 2009 (pp. 81-92).*

(Continued)

*Primary Examiner* — Jeffery A Williams
(74) *Attorney, Agent, or Firm* — Crowell & Moring LLP

(57) ABSTRACT

A method and device for monitoring at least one vehicle passenger in a vehicle involves capturing images of the vehicle passenger using an image capturing unit and analyzing the captured images using an image processing unit. At least one vital sign of the vehicle passenger is determined by the image analysis of the captured images, which can be used to operate at least one assistance device of a vehicle.

13 Claims, 1 Drawing Sheet

(51) Int. Cl.
*A61B 5/18* (2006.01)
*B60W 40/08* (2012.01)

(52) U.S. Cl.
CPC . *G06K 9/00832* (2013.01); *B60W 2040/0818* (2013.01); *B60W 2040/0872* (2013.01)

(58) Field of Classification Search
USPC .......................................................... 348/77
See application file for complete search history.

(56) References Cited

U.S. PATENT DOCUMENTS

| | | | |
|---|---|---|---|
| 2008/0294017 A1 | 11/2008 | Gobeyn et al. | |
| 2009/0231145 A1 | 9/2009 | Wada et al. | |
| 2009/0306487 A1* | 12/2009 | Crowe | A61B 5/02433 600/322 |
| 2010/0070988 A1 | 3/2010 | Cohen et al. | |
| 2010/0324437 A1 | 12/2010 | Freeman et al. | |
| 2011/0224875 A1* | 9/2011 | Cuddihy | B60K 28/06 701/42 |
| 2012/0195473 A1* | 8/2012 | De Haan | G06T 7/20 382/107 |
| 2012/0253201 A1* | 10/2012 | Reinhold | A61B 5/1113 600/473 |

FOREIGN PATENT DOCUMENTS

| | | |
|---|---|---|
| EP | 1 749 477 A1 | 2/2007 |
| JP | 8-234805 A | 9/1996 |
| JP | 2008-284165 A | 11/2008 |
| JP | 2009-213779 A | 9/2009 |
| JP | 2010-264095 A | 11/2010 |
| WO | WO 2006/064635 A1 | 6/2006 |

OTHER PUBLICATIONS

Poh, Ming-Zher et al., Non-contact, automated cardiac pulse measurements using video imaging and blind source separation,Optics Express, May 10, 2010, pp. 10762-10774, vol. 18, No. 10, Optical Society of America.*
Japanese Office Action issued in counterpart Japanese Application No. 2014-504169 dated Jul. 21, 2015, with partial English translation (Five (5) pages).
Japanese Office Action dated Nov. 18, 2014 with partial English translation (six (6) pages).
International Search Report (PCT/ISA/210) with partial English translation dated Jun. 3, 2012 (Eight (8) pages).
International Written Opinion (PCT/ISA/237) dated Jun. 3, 2012 (Six (6) pages).
German Office Action dated Jan. 18, 2012 (Eight (8) pages).
German-language Office Action issued in counterpart German Application No. 10 2011 016 772.2 dated Oct. 12, 2017 (nine pages).

* cited by examiner

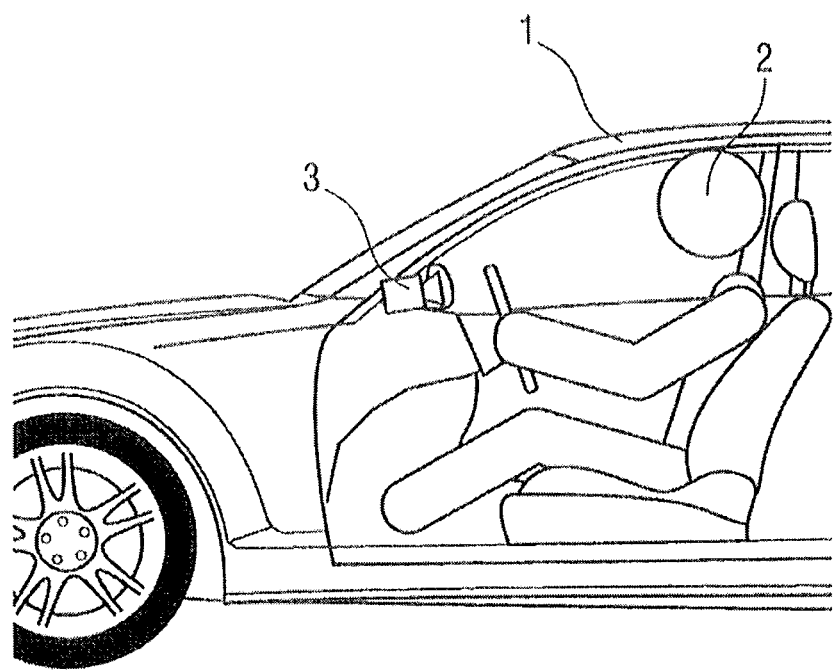

METHOD AND DEVICE FOR MONITORING AT LEAST ONE VEHICLE OCCUPANT, AND METHOD FOR OPERATING AT LEAST ONE ASSISTANCE DEVICE

BACKGROUND AND SUMMARY OF THE INVENTION

Exemplary embodiments of the present invention relate to a method and device for monitoring at least one vehicle passenger, and a method for operating at least one assistance device.

European patent document EP 1 182 089 B2 discloses a method for warning a driver of a vehicle that involves using vehicle sensors to detect a critical situation. The attention of the driver is determined, wherein an image of the driver is captured by a camera device and the image is processed by a processing unit. The attention of the driver is determined from the image, wherein the line of vision of the driver is determined by the processing unit. When the attention of the driver is determined as being high, the display of the warning is dispensed with. In the case of several warnings being displayed simultaneously, a first warning before a critical situation that lies in the line of vision of the driver is only displayed after a second warning that lies outside the line of vision of the driver.

German patent document DE 10 2009 016 936 A1, the applicant of which is the assignee of the present application and the entire contents of which are herein expressly incorporated by reference, discloses a driving assistance system to support a driver of a vehicle in the case of fatigue. The driving assistance system comprises a fatigue detection system to detect fatigue of the driver. In the case of fatigue of the driver detected by means of the fatigue detection system, a flashing warning light of the vehicle is activated to warn other road users.

Furthermore, the article by Ming-Zher Poh, Daniel J. McDuff, and Rosalind W. Picard, "Non-Contact, Automated Cardiac Pulse Measurements using Video Imaging and Blind Source Separation," Opt. Express 18, 10762-10774 (2010), the complete contents of which are expressly incorporated by reference herein, discloses a method in which, in essence, the heart rate of the person is determined by means of video sequences of faces of people, captured using low resolution video cameras. The differences in brightness of the light reflected by the skin are measured and analyzed. First, the positions of faces in the field of vision of the camera are identified, the video image in this section is broken down into red, green and blue portions and analyzed. During a heartbeat, the blood vessels—above all the arteries—expand slightly, as the pressure increases. This expansion causes an increase of the optical absorption and therefore also a decrease of the intensity of the light that is reflected by the face.

Exemplary embodiments of the present invention provide an improved method and device for monitoring at least one vehicle passenger in a vehicle and an improved method for operating at least one assistance device of a vehicle.

In a method for monitoring at least one vehicle passenger in a vehicle, images of the vehicle passenger are captured by means of at least one image capturing unit and are analyzed by means of an image processing unit.

According to the invention, at least one vital sign of the vehicle passenger is determined by the image analysis of the captured images. This enables a vital state of the vehicle passenger, for example of a driver of the vehicle, to be assessed and, in the case of a detected deterioration of the vital state, suitable measures to be taken, for example functions of an assistance device of the vehicle to be activated, in order at least to indicate a potential risk of accident or, if necessary, to prevent an accident, help to be requested and/or the comfort of the vehicle passenger(s) to be increased, in order to improve the vital state in this way. In this case, an image capturing unit already installed in the vehicle, for example in the region of a steering column, and directed towards the vehicle passenger(s), preferably towards a driver of the vehicle, preferably serves as the image capturing unit. Such image capturing units are, for example, installed to detect the attention of the driver of the vehicle. A video camera with low resolution, for example a so-called CCD camera, is sufficient to carry out the method. Special lighting equipment is also not required; ambient lighting that is normal in the vehicle, for example daylight, is sufficient.

In particular, a pulse rate or heart rate and/or a breathing rate and/or a pumping capacity of the heart and/or a blood pressure and/or an oxygen concentration in the blood of the vehicle passenger and/or autonomous bodily functions, in particular functions of an autonomous nervous system of the vehicle passenger are detected expediently as vital signs. By means of these vital signs, the current vital state of the vehicle passenger can be assessed in a sufficiently precise manner, in order to be able to suggest, for example, if necessary, an inattention of the vehicle passenger, for example of the driver of the vehicle, or a threatening or already occurring unconsciousness or a severe health problem. Advantageously, the detected vital signs are recorded and saved in the vehicle, in such a way that they are available, for example, in an emergency situation in the case of medical care. They can, for example, be transmitted to a hospital or an emergency response centre with an automatically initiated emergency call, in such a way that fast and adequate help can be initiated.

Preferably, the at least one vital sign is determined by detecting an optical absorption value and/or an intensity value of reflected light of a skin region of the vehicle passenger and/or by determining a change of this optical absorption value and/or of this intensity value. During a heartbeat, the blood vessels, in particular the arteries, expand slightly, as the pressure increases. This expansion causes an increase of the optical absorption and therefore also a decrease of the intensity of the reflected light, which is reflected by the skin region. Vital signs, in particular the pulse rate, can be determined by determining the differences in brightness of the light reflected by the skin region over the course of time. This method is also called photoplethysmography. The foundations of the method are described, for example, in the article by Ming-Zher Poh, Daniel J. McDuff, and Rosalind W. Picard, "Non-Contact, Automated Cardiac Pulse Measurements using Video Imaging and Blind Source Separation," Opt. Express 18, 10762-10774 (2010), the entire contents of which are herein expressly incorporated by reference.

Preferably, at least one region suited to image analysis is looked for in each of the images during the image processing and only this region is analyzed. This region is a region in the images, in which a sufficiently high skin region of the vehicle passenger is depicted. Preferably a region of the images is looked for and analyzed as a region suited to image analysis, which contains the face of the vehicle passenger, as in this region a sufficiently large region of skin that is able to be analyzed is available and as image capturing units, which are, in particular, already installed in the vehicle, the image capturing units being used to detect attention, are directed towards the face of the vehicle passenger, in particular of the driver of the vehicle. With the method, one or several vital signs of several vehicle passengers can be determined at the same time, wherein the image regions are determined, in which the faces of the vehicle passengers are situated and are analyzed separately from one another.

Color images are captured expediently as images of the vehicle passenger, in particular so-called RGB images, wherein the region of the images suited to image analysis is split into color channels and at least one color channel is analyzed to determine the at least one vital sign. For example, the region suited to image analysis is divided into red, green and blue portions, i.e. color channels. Therein, preferably, the green portion or color channel is analyzed, as in this color channel the precision of the achieved results is the highest.

Preferably, a spectral power density of the color channel of the image suited to image analysis is determined by means of a Fast-Fourier Transform. The differences in brightness of the light reflected by the skin region over the course of time and thus the vital sign(s) can then be determined by means of the determined spectral power density.

The vital signs determined in this way can also be combined with values of the vehicle passengers, which have been determined in a different way, in order to thus obtain a better overall picture of a state of the vehicle passenger. In this way tiredness or inattention of the driver of the vehicle can, for example, be detected early on and with a small margin of error. Thus, for example, movements of the respective vehicle passenger, in particular of the driver of the vehicle, can be detected by sensors in a vehicle seat, which can indicate restlessness, stress or the beginnings of tiredness. This can, for example, be combined with the determined pulse rate, in order to obtain a better estimation.

In a device for monitoring at least one vehicle passenger in a vehicle, in particular for carrying out the method for monitoring at least one vehicle passenger in a vehicle, images of the vehicle passenger are able to be captured by means of at least one image capturing unit and able to be analyzed by means of a image processing unit. According to the invention, at least one vital sign of the vehicle passenger is able to be determined by means of the image capturing unit through image analysis of the captured image. This enables a vital sign of the vehicle passenger, for example of a driver of the vehicle, to be assessed and, in the case of a detected deterioration of the vital state, suitable measures to be taken, for example functions of an assistance device of the vehicle to be activated, in order at least to indicate a potential risk of accident or, if necessary, to prevent an accident, help to be requested and/or the comfort of the vehicle passenger(s) to be increased, in order to improve the vital state in this way, as has already been described for the method, which is able to be carried out by means of the device, to monitor at least one vehicle passenger in a vehicle.

In a method for operating at least one assistance device of a vehicle using the method for monitoring at least one vehicle passenger, at least one function of the assistance device of the vehicle is activated if a determined value of a vital sign deviates from a predetermined value or value region for this vital sign. In this way the assistance device can intervene in a supporting manner in the case of poor or deteriorating vital signs of the vehicle passenger(s), in particular of a driver of the vehicle, in order to, for example, indicate a potential risk of accident or, if necessary, prevent an accident, request help and/or increase comfort of the vehicle passenger(s), in order to improve the vital sign in this way.

An intervention is preferably activated in a steering device, braking device and/or in a drive train of the vehicle and/or an optical, audible and/or haptic warning device as a function of the assistance device. In this way the vehicle, as described, for example, in German patent document DE 10 2009 016 936 A1 can be automatically steered to the side of the road by a corresponding intervention in the steering device, braking device and/or the drive train of the vehicle and there brought to a standstill. Particularly advantageously, the intervention in the steering device, braking device and/or in the drive train of the vehicle can occur in such a way that the vehicle can be steered autonomously to the next available emergency assistance installation, for example to the A & E department of the next available hospital.

Alternatively or additionally, the warning devices of the vehicle can be activated, for example external warning devices in the form of a flashing warning system and/or a horn of the vehicle, in order to warn other road users, and or warning devices in an interior space of the vehicle can be activated, in order to warn the vehicle passenger(s), for example in order to wake a sleeping driver of the vehicle or to indicate a poor or deteriorating vital state of the driver of the vehicle to other vehicle passengers, in such a way that these can actuate the steering wheel and/or a handbrake of the vehicle, in order to brake the vehicle and/or to steer the vehicle to the side of the road.

Alternatively or additionally, at least one comfort function and/or emergency call function is activated expediently as a function of the assistance device. By activating the comfort function or a plurality of such comfort functions, the vital signs of the vehicle passenger can be improved, for example if the determined vital parameter(s) indicate fatigue, in particular of the driver. Then, for example, a massage function of a vehicle seat, interior ventilation and/or an air conditioning function of the vehicle can be activated. In this case, essential oils or other refreshing agents can be introduced into the interior of the vehicle to refresh the vehicle passenger. Furthermore, the current vital situation can be indicated to the vehicle passenger in question by optical, audible and/or haptic means, preferably combined with a recommendation of suitable countermeasures, for example to take a refreshment break, move regularly and/or to take on sufficient fluid. The vehicle passenger can, in this way, for example, also be reminded to take required medication. Furthermore, devices of the vehicle, which support and/or calm the driver of the vehicle, can be activated in a targeted manner, for example a navigation device or an audio system of the vehicle, i.e. for example a car radio.

Additionally, the vehicle passenger can be warned of threatening health risks, for example of threatening circulation problems. In this case it is particularly advantageous to determine the vital signs of the vehicle passenger(s), for example of the driver of the vehicle, over a long period of time, for example several days or weeks, and to analyse the course thereof, in such a way that slow deteriorations can be determined. In particular in the case of older vehicle passengers and/or passengers who may be endangered or compromised in terms of health, in particular drivers of the vehicle, the sense of security and well-being thereof is considerably increased by this. In a medical emergency, an automatic emergency call can additionally be made, wherein, preferably, the detected vital signs are transmitted to an emergency call centre or a hospital, in such a way that fast and adequate medical help can be initiated. For this purpose, current positional data of the vehicle is also preferably determined and transferred with the emergency call.

BRIEF DESCRIPTION OF THE DRAWING FIGURE

Exemplary embodiments of the invention are illustrated more closely below by means of a drawing.

Therein is shown:

FIG. 1 a schematic depiction of a vehicle with a vehicle passenger and an image capturing unit directed towards them.

DETAILED DESCRIPTION

FIG. 1 shows a schematic depiction of a vehicle 1 with a vehicle passenger 2 and an image processing unit 3, which is directed towards this, as a device for monitoring the vehicle passenger. In a method for monitoring the vehicle passenger 2, images of the vehicle passenger 2 are captured by means of an image capturing unit 3, for example in the form of a video sequence, and analyzed by means of an image processing unit, which is not depicted in more detail, in order to determine at least one vital sign of the vehicle passenger 2, for example a pulse rate or heart rate and/or a breathing rate and/or a pumping capacity of the heart and/or a blood pressure and/or an oxygen concentration in the blood of the vehicle passenger 2 and/or autonomous bodily functions, in particular functions of an autonomous nervous system of the vehicle passenger 2. A vital state of the vehicle passenger 2 and an alteration of the vital state can be assessed by means of the determined vital sign(s) of the vehicle passenger 2.

The image capturing unit 3 is preferably an image capturing unit 3 that is already installed in the vehicle 1, for example, as is depicted here, in the region of a steering column, and that is directed towards the vehicle passenger 2, in the example depicted here towards a driver of the vehicle. A video camera with low resolution, for example a so-called CCD camera, is sufficient here to carry out the monitoring method. Special lighting equipment is also not required; ambient light that is normal in the vehicle 1, for example daylight, is sufficient.

The at least one vital sign is determined by detecting an optical absorption value and/or an intensity value of reflected light of a skin region of the vehicle passenger 2 and/or by detecting a change of this optical absorption value and/or this intensity value. During a heartbeat, the blood vessels, in particular the arteries, expand slightly, as the pressure increases. This expansion causes an increase of the optical absorption and therefore also a decrease of the intensity of the reflected light, which is reflected by the skin region. By detecting the differences in brightness of the light reflected by the skin region over the course of time, vital signs of the vehicle passenger 2, in particular the pulse rate or heart rate, can be determined. This method is also called photoplethysmography. The foundations of the method are described, for example, in the article by Ming-Zher Poh, Daniel J. McDuff, and Rosalind W. Picard, "Non-Contact, Automated Cardiac Pulse Measurements using Video Imaging and Blind Source Separation," Opt. Express 18, 10762-10774 (2010), the complete contents of which are included herein by reference.

During the image processing, at least one region suited to image analysis is looked for in each of the images by means of suitable methods, and only this region is analyzed. This region is a region in the images, in which a sufficiently large skin region of the vehicle passenger 2 is depicted. Preferably a region of the images is looked for and analyzed as a region suited to image analysis, which contains the face of the vehicle passenger 2, as in this region a sufficiently large region of skin that is able to be analyzed is available and as image capturing units 3, which are, in particular, already installed in the vehicle 1, the image capturing units 3 being used to detect attention, are directed towards the face of the vehicle passenger 2, in particular of the driver of the vehicle.

The location of such regions suited to image analysis is possible in images, for example, by means of facial recognition methods. With the method, one or several vital signs of several vehicle passengers 2 can be determined at the same time, if several vehicle passengers 2 are captured by the image capturing unit 3, wherein the image regions are determined, in which the faces of the vehicle passengers 2 are situated and are analyzed separated from one another.

Color images are captured as images of the vehicle passenger 2, in particular so-called RGB images, wherein the region of the images suited to image analysis is split into individual color portions or color channels, in the case of RGB images into the corresponding RGB color channels red, green and blue, and at least one color channel is analyzed to determine the at least one vital sign. Therein, preferably, the green portion or color channel is analyzed, as in this color channel the precision of the achieved result is the highest.

A spectral power density of the color channel to be analyzed of the region suited to image analysis is determined by means of Fast-Fourier Transform. Then the differences in brightness of the light reflected by the skin region in the course of time and thus the vital sign(s) of the vehicle passenger(s) 2 can be determined by means of the determined spectral power density.

The method is very simple and cost-effective for implementing and carrying out in the vehicle 1 due to the image capturing unit 3, which only has to have a low resolution, as well as due to the implementation under normal ambient light conditions, i.e. without additional special light sources. Additionally, the method is very robust with regard to different skin colors, as well as with regard to movements of the vehicle passenger(s) 2 during the capturing of the image. The determination of the vital signs is, in this case, sufficiently precise in order to be able to determine the vital state of the vehicle passenger(s) 2 as well as an alteration in the vital state by means of the determined vital parameter(s) in a sufficiently precise manner, such that a vital state, which, for example, indicates an acute emergency situation and requires medical help, or which, for example, could affect the safe driving of the vehicle 1, can be detected with a high level of certainty.

The monitoring method or the vital parameter(s) of the vehicle passenger 2, in particular of the driver of the vehicle, determined in this way, can be used in a method for operating at least one assistance device of the vehicle 1. In this case at least one function of the assistance device is activated if a determined value of a vital sign deviates from a predetermined value or value region for this vital sign.

In this way the assistance device can intervene in a supporting manner in the case of poor or deteriorating vital signs of the vehicle passenger(s) 2, in particular of the driver of the vehicle, in order to, for example, prevent an accident, request help and/or increase comfort of the vehicle passenger(s) 2, in order to thus improve the vital state.

An intervention is preferably activated in a steering device, braking device and/or in a drive train of the vehicle 1 and/or an optical, audible and/or haptic warning device as an assistance device. In this way, the vehicle 1, as described, for example, in German patent document DE 10 2009 016 936 A1 can be, for example, automatically steered to the side of the road by a corresponding intervention in the steering device, braking device and/or the drive train of the vehicle 1 and there brought to a standstill. Particularly advantageously, the intervention in the steering device, braking device and/or in the drive train of the vehicle 1 can occur in such a way that the vehicle 1 is steered autonomously to the next available emergency assistance installation, for example to the A & E department of the next available hospital.

Alternatively or additionally, warning devices of the vehicle 1 can be activated, for example external warning devices in the form of a flashing warning system and/or a horn of the vehicle 1, in order to warn other road users, and/or warning devices in an interior space of the vehicle can be activated, in order to warn the vehicle passenger(s) 2, for example in order to wake a sleeping driver of the vehicle or to indicate poor or deteriorating vital signs of the driver of the vehicle to other vehicle passengers 2, which possibly indicate a deteriorating state of health, in such a way that these can actuate, for example, the steering wheel and/or a handbrake of the vehicle 1, in order to brake the vehicle 1 and/or to steer the vehicle 1 to the side of the road.

Alternatively or additionally, at least one comfort function and/or emergency call function is activated expediently as a function of the assistance device. By activating the comfort function or a plurality of such comfort functions, the vital signs of the vehicle passenger(s) 2 can be improved, for example if the determined vital parameter(s) indicate fatigue, in particular of the driver.

Then, for example, a massage function of a vehicle seat, interior ventilation and/or an air conditioning function of the vehicle 1 can be activated. In this case, essential oils or another refreshing medium can be introduced into the interior of the vehicle 1 to refresh the vehicle passenger(s) 2. Furthermore, the current vital situation can be indicated to the vehicle passenger 2 in question by optical, audible and/or haptic means, preferably combined with a recommendation of suited countermeasures, for example to take a refreshment break, to move regularly and/or to take on sufficient fluid. The vehicle passenger 2 can, in this way, for example, also be reminded to take required medication. Furthermore, for example in the case of an increased stress level, detected by means of the vital signs, devices of the vehicle 1, which support and/or calm the driver of the vehicle, can be activated in a targeted manner, for example a navigation device or an audio system of the vehicle 1, i.e. for example a car radio.

Additionally, the vehicle passengers 2 can be warned of threatening health risks, for example of threatening circulation problems. In particular in the case of older vehicle passengers 2, and/or passengers who may be endangered or compromised in terms of health, in particular drivers of the vehicle, the sense of security and well-being thereof is considerably increased. In a medical emergency, an automatic emergency call can additionally be made, wherein, preferably, the detected and saved vital signs are transmitted to an emergency call center or a hospital, in such a way that fast and adequate medical help can be initiated. For this purpose, current positional data of the vehicle 1 is also preferably determined and transferred with the emergency call.

The vital signs determined by means of the monitoring method can also be combined with values of the vehicle passenger(s) 2, determined in a different way, in order to thus obtain a better overall picture of a state of the vehicle passenger(s) 2. In this way tiredness or inattention of the driver of the vehicle can, for example, be detected early on and with a small margin of error. Thus, for example, movements of the respective vehicle passenger 2, in particular of the driver of the vehicle, can be detected by sensors in a vehicle seat, which can indicate restlessness, stress or the beginnings of tiredness. Additionally, the inattention detecting function for which the image capturing unit is primarily installed in the vehicle 1 can be used. In this way, detected additional values of the vehicle passenger(s) 2 can, for example, be combined with the detected pulse rate, in order to obtain a better estimation of the vital state of the vehicle passenger(s) 2.

A simple black and white camera can be used as an image capturing unit, e.g. in order to obtain a more robust analysis. An infra-red camera can also be used as an image capturing unit, in order to detect the vital signs in dark areas of the roads or in darkness. A switchover to the infra-red region can automatically be carried out by means of brightness detection, as is used in the case of the automatic driving light control.

As has already been mentioned, in particular the green portion or color channel is preferably analyzed, as in this color channel the precision of the achieved result is the highest. With the use of a color camera, the robustness can be increased, if all three RGB components of the image signal are analyzed in a weighted manner, as all 3 RGB channels carry redundant information to the measured vital signs.

An advantage of the implemented method id that both the pulse and the breathing rate can be determined with one and the same image signal from the face region. A rotation of the camera to the chest region is not necessary in order to measure the breathing rate. In general it is not necessary to switch the camera between face, chest or other bodily regions.

As has already been mentioned, special lighting devices are not required, as ambient light that is normal in the vehicle, for example daylight, is sufficient. A feasibility analysis shows that missing image sequences, e.g. during travel in dark areas of road, such as heavily shadowed sections of road, e.g. under bridges or tunnels, have no negative influence on the comprehensive analysis of the state of the driver during the day, if it is only for short periods of time (a few minutes). For longer periods of darkness during the day or at night, the use of an infra-red camera is required in order to record the data for the image processing. The images produced in this are of the same quality as the images of a black and white camera. This is, however, not a restriction, because the method can also handle black and white images in a robust manner.

It will be recognized that the "Fast-Fourier Transform" is commonly referred to as FFT.

It has already been mentioned that, with the described method, inattention of the vehicle passenger, for example of the driver of the vehicle, or a threatening or already occurring unconsciousness or a severe health problem can be suggested. Moreover the contactless measuring of the vital data offers a diagnostic value for a) tachycardia, brachycardia, bradycardia, b) heart rate variability (to distinguish e.g. calm, stress, elation) and c) the detection of tendencies towards viral infection (skin temperature, pulse, breathing rate).

It has been described that at least one function of the assistance device is activated if a determined value of a vital sign deviates from a predetermined value or value region for this vital parameter. A combination of the determined vital signs with values of the vehicle passengers (such as attention, unrest, tiredness, stress) determined in other ways can, however, also be used to activate at least one comfort function, emergency function or recommendation of countermeasures. Such recommendations can be taking a refreshment break, moving regularly, taking on sufficient fluids or taking a required medication.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A method for monitoring at least one vehicle passenger in a vehicle, the method comprising:
   capturing images of the vehicle passenger using at least one camera directed toward a first bodily region;
   analyzing the captured images of the first bodily region using at least one processor;
   determining a first vital sign and a second vital sign different from the first vital sign of the vehicle passenger, the determining of each of the first and second vital signs being based on the image analysis of the captured images;
   determining, based on the determined first vital sign and the second vital sign, one or more diagnostic values for: (i) tachycardia or bradycardia, (ii) heart rate variability, and (iii) tendency related to viral infection; and
   recommending a suitable countermeasure based at least on the determined one or more diagnostic values,
   wherein the determined first vital sign is a pulse rate and the second vital sign is a breathing rate, and
   wherein the first vital sign and the second vital sign are both determined from the same captured images of the first bodily region so that it is unnecessary to move or rotate the at least one camera toward a second bodily region to determine the second vital sign.

2. The method according to claim 1, wherein one or more of the first and second vital signs is determined by
   detecting an optical absorption value or an intensity value of reflected light of a skin region of the vehicle passenger, or
   calculating a change of the optical absorption value or of the intensity value.

3. The method according to claim 1, wherein during image processing for analyzing the captured images, at least one region suited to image analysis is looked for in each of the captured images and only the at least one region suited to image analysis is analyzed.

4. The method according to claim 3, wherein the at least one region suited to image analysis contains a face of the vehicle passenger.

5. The method according to claim 3, wherein the captured images of the vehicle passenger are color, wherein the region of the images suited to image analysis is split into individual color channels and at least one of the individual color channels is analyzed to determine one or more of the first and second vital signs.

6. The method according to claim 5, wherein a spectral power density of the at least one of the individual color channels of the region suited to image analysis is determined using a Fast-Fourier Transform.

7. A device for monitoring at least one vehicle passenger in a vehicle, the device comprising:
   at least one camera directed toward a first bodily region and configured to capture images of the vehicle passenger; and
   at least one processor executing stored instructions to:
      analyze the captured images of the first bodily region,
      determine a first vital sign and a second vital sign different from the first vital sign of the vehicle passenger, the determination of each of the first and second vital signs being based on image analysis of the captured images,
      determine, based on the determined first vital sign and the second vital sign, one or more diagnostic values for: (i) tachycardia or bradycardia, (ii) heart rate variability, and (iii) tendency related to viral infection, and
      recommend a suitable countermeasure based at least on the determined one or more diagnostic values,
   wherein the determined first vital sign is a pulse rate and the second vital sign is a breathing rate, and
   wherein the first vital sign and the second vital sign are both determined from the same captured images of the first bodily region so that it is unnecessary to move or rotate the at least one camera toward a second bodily region to determine the second vital sign.

8. A method, comprising:
   capturing images of a vehicle passenger in a vehicle using at least one camera directed toward a first bodily region;
   analyzing the captured images of the first bodily region using at least one processor;
   determining a first vital sign and a second vital sign different from the first vital sign of the vehicle passenger, the determining of each of the first and second vital signs being based on the image analysis of the captured images;
   determining, based on the determined first vital sign and the second vital sign, one or more diagnostic values for: (i) tachycardia or bradycardia, (ii) heart rate variability, and (iii) tendency related to viral infection; and
   activating at least one function of an assistance device if a determined value of one or more of the first and second vital signs deviates from a predetermined value or value region and recommending a suitable countermeasure based at least on the determined one or more diagnostic values,
   wherein the determined first vital sign is a pulse rate and the second vital sign is a breathing rate, and
   wherein the first vital sign and the second vital sign are both determined from the same captured images of the first bodily region so that it is unnecessary to move or rotate the at least one camera toward a second bodily region to determine the second vital sign.

9. The method according to claim 8, wherein an intervention in a steering device, braking device, or in a drive train of the vehicle, an optical, audible, or haptic warning device, or at least one comfort function or an emergency function is activated as a function of the assistance device.

10. The method according to claim 1, further comprising the step of distinguishing whether the first vital sign indicates calm, stress, or elation based on the one or more diagnostic values related to the heart rate variability.

11. The method according to claim 1, wherein the suitable countermeasure includes one or more of the following: (i) taking a refreshment break, (ii) moving regularly, (iii) taking sufficient fluid, and (iv) taking required medication.

12. The method according to claim 1, further comprising activating at least one function of one or more devices of the vehicle based on the determined first vital sign and the second vital sign.

13. The method according to claim 1, further comprising providing the recommendation of the suitable countermeasure to the at least one vehicle passenger of the vehicle via one or more devices of the vehicle and the at least one vehicle passenger acting on the recommendation based on the recommendation provided by the one or more devices of the vehicle.

* * * * *